(12) United States Patent
Kim et al.

(10) Patent No.: US 11,564,626 B2
(45) Date of Patent: Jan. 31, 2023

(54) IMPLANTABLE MONITORING DEVICE AND METHOD OF OPERATING THE IMPLANTABLE MONITORING DEVICE

(71) Applicants: Samsung Electronics Co., Ltd., Suwon-si (KR); POSTECH Research and Business Development Foundation, Pohang-si (KR)

(72) Inventors: Jonghan Kim, Seoul (KR); Sung Min Park, Seongnam-si (KR); Jun Ho Kim, Yongin-si (KR); Young Jun Hong, Seoul (KR); Jongpal Kim, Seoul (KR)

(73) Assignees: Samsung Electronics Co., Ltd., Suwon-si (KR); POSTECH Research and Business Development Foundation, Pohang-si (KR)

(*) Notice: Subject to any disclaimer, the term of this patent is extended or adjusted under 35 U.S.C. 154(b) by 313 days.

(21) Appl. No.: 16/721,972

(22) Filed: Dec. 20, 2019

(65) Prior Publication Data
US 2021/0059606 A1    Mar. 4, 2021

(30) Foreign Application Priority Data

Aug. 26, 2019   (KR) .................. 10-2019-0104596

(51) Int. Cl.
*A61B 5/0205*   (2006.01)
*A61B 5/00*     (2006.01)
(Continued)

(52) U.S. Cl.
CPC .......... *A61B 5/6847* (2013.01); *A61B 5/0006* (2013.01); *A61B 5/0538* (2013.01);
(Continued)

(58) Field of Classification Search
CPC ..... A61B 5/021; A61B 5/4818; A61B 5/6847; A61B 5/1116; A61B 5/1102
See application file for complete search history.

(56) References Cited

U.S. PATENT DOCUMENTS 8,731,653 B2   5/2014   Patterson et al.
9,737,262 B2   8/2017   Donnelly et al.
(Continued)

FOREIGN PATENT DOCUMENTS

JP   2019-509476 A   4/2019
JP   6511481 B2      5/2019
KR   10-1182994 B1   9/2012

*Primary Examiner* — Michael J D'Abreu
(74) *Attorney, Agent, or Firm* — NSIP Law

(57) ABSTRACT

An implantable monitoring device includes first sensors to measure state information of one or both of a posture and an activity of a user and second sensors to measure bioinformation of two or more of an electrocardiogram (ECG) of a heart of the user, a pulmonary impedance of a lung of the user, a movement of the heart, a movement of a thorax including the lung, and a respiratory quotient (RQ) of the lung, two electrodes to detect bioinformation to measure one or both of the ECG and the pulmonary impedance, an analog circuit to process the detected bioinformation to measure the one or both of the ECG and the pulmonary impedance, and a processor to monitor an abnormal state of the heart and the lung of the user based on the state information and the bioinformation.

19 Claims, 7 Drawing Sheets

(51) Int. Cl.
  *A61B 5/11* (2006.01)
  *A61B 5/0538* (2021.01)
  *A61B 5/08* (2006.01)
  *A61B 5/283* (2021.01)

(52) U.S. Cl.
  CPC .......... *A61B 5/0809* (2013.01); *A61B 5/1102* (2013.01); *A61B 5/1116* (2013.01); *A61B 5/1118* (2013.01); *A61B 5/283* (2021.01); *A61B 2560/0219* (2013.01); *A61B 2562/0247* (2013.01)

(56) References Cited

U.S. PATENT DOCUMENTS

| | | | |
|---|---|---|---|
| 2005/0061320 A1* | 3/2005 | Lee | A61M 16/00 128/204.18 |
| 2005/0085734 A1 | 4/2005 | Tehrani | |
| 2006/0241701 A1 | 10/2006 | Markowitz et al. | |
| 2009/0048644 A1 | 2/2009 | Stahmann et al. | |
| 2011/0009746 A1 | 1/2011 | Tran et al. | |
| 2012/0245439 A1* | 9/2012 | Andre | G16H 40/67 600/595 |
| 2019/0110684 A1 | 4/2019 | Coen et al. | |

\* cited by examiner

100

FIG. 4
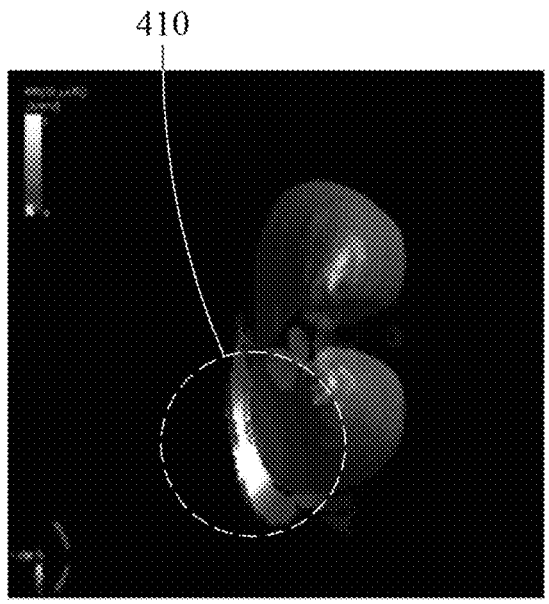 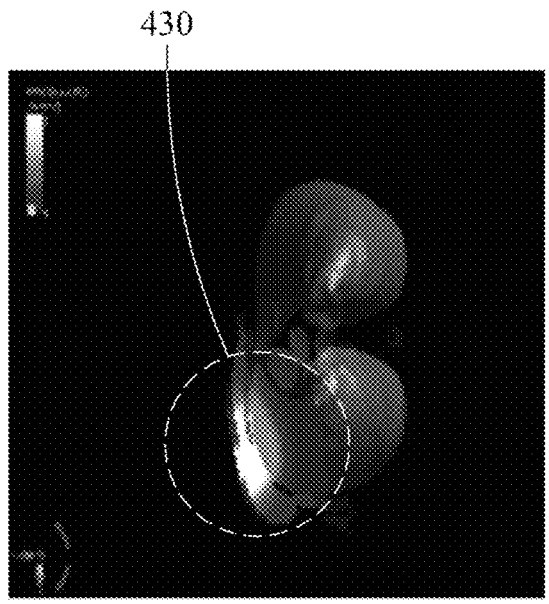
Normal lung — Lung with pulmonary edema

IMPLANTABLE MONITORING DEVICE AND METHOD OF OPERATING THE IMPLANTABLE MONITORING DEVICE

CROSS-REFERENCE TO RELATED APPLICATIONS

This application claims the benefit under 35 USC § 119(a) of Korean Patent Application No. 10-2019-0104596 filed on Aug. 26, 2019, in the Korean Intellectual Property Office, the entire disclosure of which is incorporated herein by reference for all purposes.

BACKGROUND

1. Field

The following description relates to an implantable monitoring device and a method of operating the implantable monitoring device.

2. Description of Related Art

Heart failure, or congestive cardiac failure, occurs when a mechanical pumping function of a heart is degraded, and thus the heart is unable to sufficiently supply blood to the entire body. Such a condition may become serious, with its five-year survival rate after the outbreak being 50% or less which is lower than that of a cancer. Heart failure may weaken the heart function and increase a risk of sudden death and arrhythmia, and be intractable and thus not be completely cured. Thus, this condition may need to be monitored and managed thoroughly. For a patient with heart failure may need self-care management such as continuous monitoring of a physical condition. However, the monitoring involves a medical or surgical procedure of inserting a lead electrode into a heart, which has become more complicated and poses a growing risk of infection.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an implantable monitoring device includes first sensors configured to measure state information of one or both of a posture and an activity of a user, and second sensors configured to measure bioinformation of two or more of an electrocardiogram (ECG) of a heart of the user, a pulmonary impedance of a lung of the user, a movement of the heart, a movement of a thorax including the lung, and a respiratory quotient (RQ) of the lung, two electrodes configured to detect bioinformation to measure one or both of the ECG and the pulmonary impedance, an analog circuit configured to process the detected bioinformation to measure the one or both of the ECG and the pulmonary impedance, and a processor configured to monitor an abnormal state of the heart and the lung of the user based on the state information of the one or both of the posture and the activity of the user and the bioinformation of the two or more of the ECG, the pulmonary impedance, the movement of the heart, the movement of the thorax, and the RQ.

The implantable monitoring device may be implanted into a subcutaneous fat layer within a preset distance from the heart and the lung on one side. The second sensors may include a potential sensor configured to sense a potential difference between the electrodes at an implantation position in which the implantable monitoring device is implanted, to measure the one or both of the ECG and the pulmonary impedance, and a pressure sensor configured to sense a pressure at the implantation position to measure one or more of the movement of the heart, the movement of the thorax, and the RQ.

The analog circuit may include one or more of a current generator configured to generate an alternating current (AC) to measure the pulmonary impedance, a voltage amplifier configured to amplify an AC voltage between the electrodes, and an analog-to-digital converter (ADC) configured to convert an analog signal based on the AC voltage to a digital signal based on a direct current (DC) voltage.

The analog circuit may obtain the pulmonary impedance by analyzing an AC voltage between the electrodes measured when the AC generated through the current generator is supplied, and obtain the ECG by analyzing an AC voltage between the electrodes measured when the AC is not supplied.

The processor may monitor the abnormal state of the heart based on two or more of the ECG, the pulmonary impedance, or the movement of the heart based on the state information.

When the ECG is in a normal range and the movement of the heart and the RQ of the lung are out of a normal range based on the state information, the processor may transmit a signal indicating a possibility of occurrence of a valvular disease in the heart of the user.

When the pulmonary impedance measured when the posture of the user is a lying posture is less than a normal range, the processor may transmit a signal indicating a possibility of occurrence of heart failure in the heart of the user.

The processor may monitor the abnormal state of the lung based on one or more of the pulmonary impedance, the movement of the thorax, and the RQ based on the state information.

When the RQ measured when the posture of the user is a lying posture is greater than a normal RQ or the pulmonary impedance measured when the posture of the user is the lying posture is less than a normal range, the processor may transmit a signal indicating a possibility of occurrence of pulmonary edema in the lung of the user.

The processor may monitor the abnormal state of the heart and the lung of the user based on a result of comparing the bioinformation of the two or more of the ECG, the pulmonary impedance, the movement of the heart, the movement of the thorax, and the RQ, and a reference value of bioinformation of the two or more of the ECG, the pulmonary impedance, the movement of the heart, the movement of the thorax, and the RQ that is classified by each posture and activity of the user.

The implantable monitoring device may further include a database (DB) configured to classify the bioinformation of the two or more of the ECG, the pulmonary impedance, the movement of the heart, the movement of the thorax, and the RQ by each posture and activity of the user, and store the classified bioinformation.

A measurement period of the first sensors and the second sensors may be preset.

The implantable monitoring device may further include one or more of a communication antenna configured to transmit a result of the monitoring, a wireless power transfer antenna configured to receive energy wirelessly, and a power management circuit configured to charge a battery configured to supply power to the implantable monitoring device using the energy.

The first and second sensors may include three or more of a motion sensor configured to measure one or both of the posture and the activity of the user, an ECG sensor configured to measure an electrical signal of the heart of the user, an impedance sensor configured to measure the pulmonary impedance of the lung of the user, and a pressure sensor configured to measure one or more of the movement of the heart, the movement of the thorax, and the RQ.

In another general aspect, a method of operating an implantable monitoring device includes measuring state information of one or both of a posture and an activity of a user, measuring bioinformation of two or more of an ECG of a heart of the user, a pulmonary impedance of a lung of the user, a movement of the heart, a movement of a thorax including the lung, and an RQ of the lung, detecting bioinformation to measure one or both of the ECG and the pulmonary impedance, processing the detected bioinformation to measure the one or both of the ECG and the pulmonary impedance, and monitoring an abnormal state of the heart and the lung of the user based on the state information of the one or both of the posture and the activity of the user and the bioinformation of the two or more of the ECG, the pulmonary impedance, the movement of the heart, the movement of the thorax, and the RQ.

The implantable monitoring device may be implanted into a subcutaneous fat layer within a preset distance from the heart and the lung on one side, and include two electrodes. The measuring of the bioinformation of the two or more of the ECG, the pulmonary impedance, the movement of the heart, the movement of the thorax, and the RQ may include sensing a potential difference between the electrodes at an implantation position in which the implantable monitoring device is implanted, to measure the one or both of the ECG and the pulmonary impedance, and sensing a pressure at the implantation position to measure one or more of the movement of the heart, the movement of the thorax, and the RQ.

The processing of the bioinformation may include obtaining the pulmonary impedance by analyzing an AC voltage between the electrodes measured when an AC generated through a current generator of the implantable monitoring device is supplied, and obtaining the ECG by analyzing an AC voltage between the electrodes measured when the AC is not supplied.

The monitoring of the abnormal state of the heart and the lung of the user may include monitoring the abnormal state of the heart based on two or more of the ECG, the pulmonary impedance, and the movement of the heart based on the state information.

The monitoring of the abnormal state of the heart and the lung of the user may include monitoring the abnormal state of the lung based on one or more of the pulmonary impedance, the movement of the thorax, and the RQ based on the state information.

Other features and aspects will be apparent from the following detailed description, the drawings, and the claims.

BRIEF DESCRIPTION OF THE DRAWINGS

FIG. 4 illustrates an example of an impedance of a normal lung and an example of an impedance of a lung with pulmonary edema.

Figure 1:
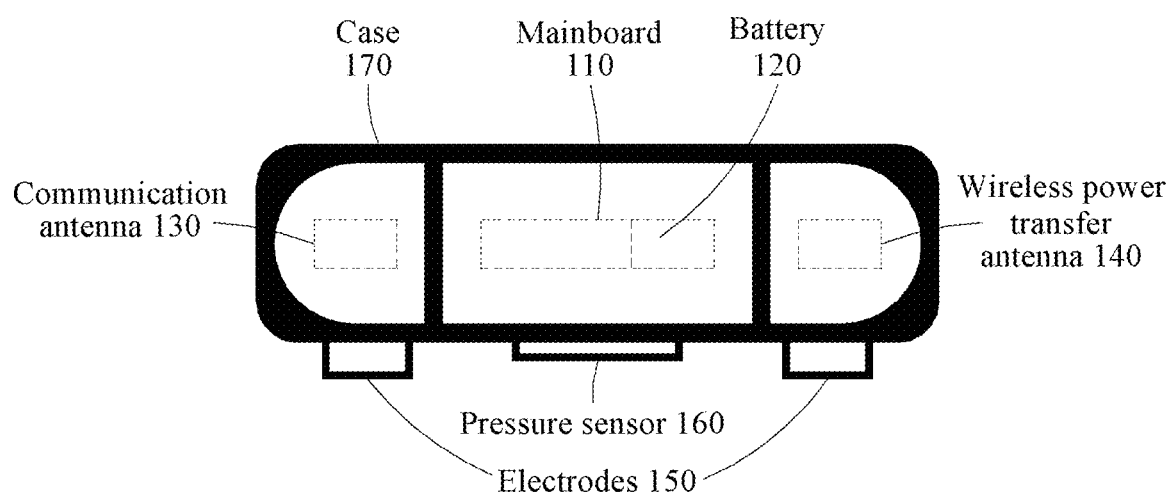
FIG. 1 illustrates an example of a layout of an implantable monitoring device.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after an understanding of the disclosure of this application may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when a component is described as being "connected to," or "coupled to" another component, it may be directly "connected to," or "coupled to" the other component, or there may be one or more other components intervening therebetween. In contrast, when an element is described as being "directly connected to," or "directly coupled to" another element, there can be no other elements intervening therebetween. Likewise, similar expressions, for example, "between" and "immediately between," and "adjacent to" and "immediately adjacent to," are also to be construed in the same way. As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

The terminology used herein is for describing various examples only and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Unless otherwise defined, all terms, including technical and scientific terms, used herein have the same meaning as commonly understood by one of ordinary skill in the art to which this disclosure pertains and based on an understanding of the disclosure of the present application. Terms, such as those defined in commonly used dictionaries, are to be interpreted as having a meaning that is consistent with their meaning in the context of the relevant art and the disclosure of the present application and are not to be interpreted in an idealized or overly formal sense unless expressly so defined herein. The use of the term "may" herein with respect to an example or embodiment (e.g., as to what an example or embodiment may include or implement) means that at least one example or embodiment exists where such a feature is included or implemented, while all examples are not limited thereto.

Also, in the description of examples, detailed description of structures or functions that are thereby known after an understanding of the disclosure of the present application will be omitted when it is deemed that such description will cause ambiguous interpretation of the example embodiments.

Hereinafter, examples will be described in detail with reference to the accompanying drawings, and like reference numerals in the drawings refer to like elements throughout.

FIG. 1 illustrates an example of a layout of an implantable monitoring device. Referring to FIG. 1, an implantable monitoring device 100 includes a mainboard 110, a battery 120, a communication antenna 130, a wireless power transfer antenna 140, electrodes 150, a pressure sensor 160, and a case 170.

The mainboard 110 includes an analog circuit configured to obtain information and process the obtained information to measure, for example, an electrocardiogram (ECG) and/or a pulmonary impedance, a processor configured to process the information and transmit the processed information, motion sensors, and a power management circuit. A configuration of the mainboard 110 will be described in greater detail with reference to FIG. 2.

The battery 120 supplies power to the implantable monitoring device 100, and may be a secondary battery that is rechargeable, such as, for example, a nickel-cadmium battery, a lithium-ion battery, a nickel-hydride battery, and a lithium-polymer battery. In an example, it is possible to reduce a size of the implantable monitoring device 100 by reducing a size of the battery 120, and supply energy through wireless power transfer. In this example, using an extremely small battery, it is possible to reduce the size of the implantable monitoring device 100 to facilitate implantation and minimize inconvenience after the implantation.

The communication antenna 130 may be a radio frequency (RF) communication antenna. The communication antenna 130 radiates, as an electromagnetic wave into air, an alternating current (AC) voltage that is modulated by a transmitter-receiver (refer to the reference numeral 260 in FIG. 2) of the implantable monitoring device 100 for communication between the implantable monitoring device 100 and an external receiver (refer to the reference numeral 203 in FIG. 2), and radiates a wave obtained by converting a received electromagnetic wave to an AC voltage.

The wireless power transfer antenna 140 may also be referred to as a wireless energy transmission antenna, and transmits and receives electrical energy without a wire. The wireless power transfer antenna 140 wirelessly receives energy through magnetic induction (MI), magnetic resonance (MR), and/or long-distance microwaves, for example. In an example, through the wireless power transfer, it is possible to semi-permanently use the implantable monitoring device 100 or the battery 120 without replacement.

The electrodes 150 detect bioinformation to measure the ECG and/or the pulmonary impedance. For example, each of the electrodes 150 may have a size of 0.5×0.5×0.5 millimeters (mm), and the electrodes 150 may be disposed separate from each other by 30 mm.

The pressure sensor 160 is disposed outside the implantable monitoring device 100, and measures a movement of a thorax including a lung, a movement of a heart, and/or a respiratory quotient (RQ) of the lung.

The case 170 is completely sealable and formed of titanium, for example.

The implantable monitoring device 100 may be implanted under thoracic skin, for example, and configured to collect and/or transmit various sets of bioinformation, monitor a physical state using the collected bioinformation, and notify a user or a doctor of an abnormal state when discovered by the monitoring.

Figure 2:
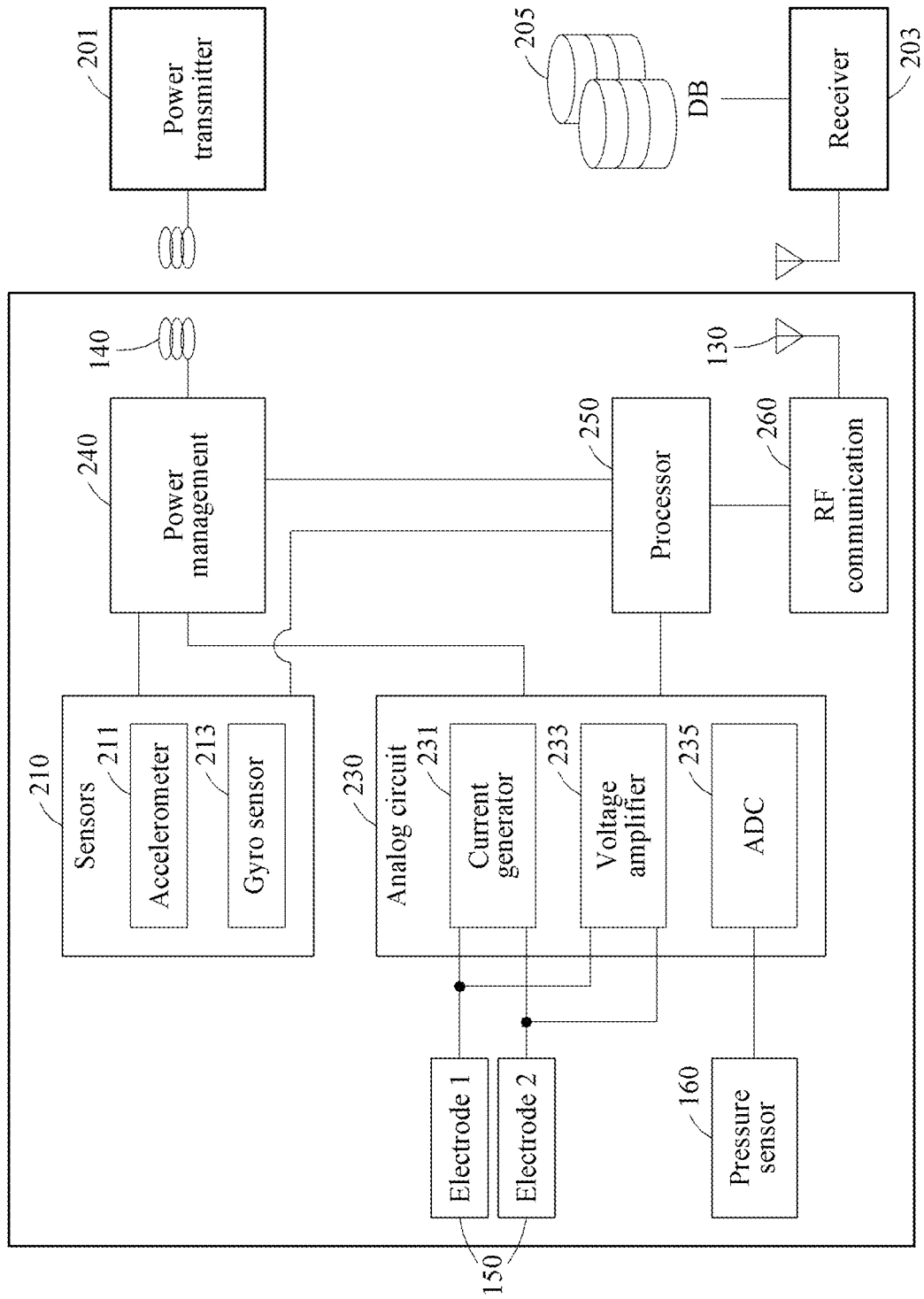
FIG. 2 illustrates an example of a configuration of an implantable monitoring device.

FIG. 2 illustrates an example of a configuration of an implantable monitoring device. Referring to FIG. 2, an implantable monitoring device 200 includes a plurality of sensors 210, a pressure sensor 160, an analog circuit 230, two electrodes 150, a power management circuit 240, a processor 250, and a transmitter-receiver 260. The sensors 210, the analog circuit 230, the power management circuit 240, the processor 250, the transmitter-receiver 260, a communication antenna 130, a wireless power transfer antenna 140, the two electrodes 150, and the pressure sensor 160 may all be electrically connected.

The sensors 210 includes a plurality of first sensors configured to measure state information of at least one of a posture or an activity of a user, and a plurality of second sensors configured to measure bioinformation of at least two of an ECG of a heart of the user, a pulmonary impedance of a lung of the user, a movement of the heart, a movement of thorax including the lung, or an RQ of the lung. The first sensors may be motion sensors configured to sense a movement of the user and including, for example, an accelerometer 211 and a gyro sensor 213 as illustrated. The second sensors may include, for example, a potential sensor and/or the pressure sensor 160 as illustrated. The potential sensor may sense a potential difference between the electrodes 150 at an implantation position in which the implantable monitoring device 200 is implanted, to measure at least one of an ECG or a pulmonary impedance. The potential sensor may include, for example, an ECG sensor configured to measure an electrical signal of the heart of the user, and an impedance sensor configured to measure the pulmonary impedance of the user. The ECG sensor and the impedance sensor may be embodied as a single sensor. The sensors 210 may further include a body temperature sensor.

A measurement period of the first sensors and/or the second sensors may be set in advance, and the implantable monitoring device 200 may continuously collect the bioinformation through the sensors 210.

The pressure sensor 160 may sense a pressure at the implantation position to measure at least one of the movement of the heart of the user, the movement of the thorax, or the RQ.

For example, the movement of the thorax that is sensed through the pressure sensor 160 may be obtained as a low-frequency baseline, and the movement of the heart may be obtained as being included in the low-frequency baseline. In this example, the movement of the heart and the movement of the thorax may be identified from each other by a size and a frequency of each of the movements. For example, when a size of a movement of the user is relatively large, for example, as when the user is doing exercise, the size of the movement of the thorax may also be large. When the size of the movement of the user is relatively small, for example, as when the user is sitting in a set posture or lying in a recumbent posture, the size of the movement of the thorax may also be small. When the size of the movement of the thorax increases, a length of one respiration interval may decrease and $\Delta R/R0$ per unit time may increase rapidly. In $\Delta R/R0$, R0 denotes a respiration volume obtained when there is not movement of a user, and $\Delta R$ denotes a variation in respiration volume based on a movement of the user.

The RQ may refer to a ratio between a volume of oxygen $O_2$ consumed by a human body in a given time and a volume of carbon dioxide $CO_2$ expired by the human body in the given time. The RQ may be obtained by dividing the volume of $CO_2$ expired by the volume of $O_2$ consumed (volume of $CO_2$ expired/volume of $O_2$ consumed). The RQ may be calculated by obtaining analytical data by allowing data of the movement of the thorax detected from the pressure sensor 160 to pass through a low-pass filter (LPF), detecting peak values from the obtained analytical data, and then calculating an interval between the peak values. For example, the implantable monitoring device 200 may obtain the analytical data, for example, a waveform corresponding to each of systole and diastole in each cardiac cycle, by allowing the data of the movement of the thorax to pass through the LPF. Thus, the implantable monitoring device 200 may calculate the RQ based on an interval of peak values detected in each cardiac cycle.

The analog circuit 230 may process bioinformation to measure at least one of the ECG and the pulmonary impedance. For example, the analog circuit 230 includes a current generator 231, a voltage amplifier 233, and an analog-to-digital converter (ADC) 235 as illustrated.

The current generator 231 may generate an AC to measure the pulmonary impedance. The analog circuit 230 may obtain the pulmonary impedance of the lung of the user by analyzing an AC voltage between the electrodes 150 measured when the AC generated by the current generator 231 is applied to a body of the user. The electrodes 150 may detect bioinformation to measure at least one of the ECG or the pulmonary impedance.

The body may consist of biological tissues having various electrical properties. A biological tissue may have conductivity through ions capable of carrying charges. A biological tissue may have different conductivity based on a portion of the body. For example, a biological tissue such as muscle may have a property of a conductor through which a current flows, whereas a biological tissue such as bone may have a property of a nonconductor through which a current does not flow well. In addition, a biological tissue may have electrical resistivity. Since a magnitude of the AC supplied to the body of the user may be information that is known, the pulmonary impedance may be obtained by analyzing the AC voltage measured based on Ohm's law, for example, $Z=V/I$, in which Z, V, and I denote an impedance, a voltage, and a current, respectively. The pulmonary impedance may not be a value that varies greatly from 0 to a maximum value, but a value that varies within a small variation range based on a set impedance value of a large direct current (DC) component. The implantable monitoring device 200 may measure an amount of a fluid filled in the lung by measuring the pulmonary impedance, and generate and transmit a signal indicating a possibility of occurrence of pulmonary edema in the lung based on the measured amount.

The analog circuit 230 may obtain the ECG by analyzing an AC voltage between the electrodes 150 measured when an AC is not supplied.

The voltage amplifier 233 may amplify the AC voltage between the electrodes 150.

The ADC 235 may convert an analog signal based on the AC voltage amplified by the voltage amplifier 233 to a digital signal based on a DC voltage.

The power management circuit 240 may convert a voltage of a battery to a voltage that may be used by other components. The power management circuit 240 may charge the battery configured to supply power to the implantable monitoring device 200 using energy received from an external power transmitter 201.

The processor 250 may control an overall operation of the implantable monitoring device 200. The processor 250 may control the current generator 231 of the analog circuit 230, and receive the digital signal that is obtained by the conversion through the ADC 235 from the state information and the bioinformation obtained from the sensors 210 and the voltage amplifier 233. The processor 250 may transmit, to an external receiver 203 through the communication antenna 130, the state information and the bioinformation that are converted to the digital signal. The external receiver 203 may store, in a database (DB) 205, data received from the processor 250 and monitor an activity and a physical state of the user using the stored data. The processor 250 may continuously collect state information and bioinformation of the user and determine a change of the bioinformation of the user, and thus diagnose a health state or predict a possibility of occurrence of a disease.

The processor 250 may monitor an abnormal state of the heart and the lung of the user based on the state information and the bioinformation processed in the analog circuit 230. Since heart failure and pulmonary edema are related to each other, collectively combining and considering various sets of bioinformation may enable more accurate monitoring.

The processor 250 may monitor an abnormal state of the heart of the user based on at least two of the ECG, the pulmonary impedance, or the movement of the heart based on the state information. The abnormal state of the heart of the user may indicate a state of the heart in which a disease such as, for example, arrhythmia, heart failure, and heart valve abnormality occurs in the heart of the user. The processor 250 may transmit a result of the monitoring to the external receiver 203.

For example, when the ECG is in a normal range and the movement of the heart and the RQ of the lung are out of a normal range based on state information, the processor 250 may determine a possibility of occurrence of a valvular disease in the heart and transmit a signal indicating the possibility of the occurrence of the valvular disease. In this example, the normal range may be construed as being a range including values within an error range (for example, 2%) from a reference value based on cumulative bioinformation classified by each posture and activity of the user, an initial measurement value obtained in a normal state of the user, or a measurement value obtained from a normal or healthy body based on medical data. The posture of the user may be construed as being a shape or a form of the body of the user that is taken when the user is standing, sitting, lying, bending his/her back, and folding legs or arms, for example. The activity of the user may correspond to an action performed by the user by moving his/her body, for example, sleeping, not moving, walking, running, and the like. Thus, although the user is in the normal state, bioinformation of the user may have a value that varies by each posture and activity of the user. Thus, in an example, whether the heart and the lung of the user is in the abnormal state may be monitored based on bioinformation classified by each posture and activity of the user. In addition, based on the activity of the user, bioinformation may be selectively used with external factors excluded.

For example, when the pulmonary impedance measured when the user is lying is less than a normal range or decreases gradually, the processor 250 may determine a possibility of occurrence of heart failure in the heart, and transmit a signal indicating the possibility of occurrence of heart failure.

The processor 250 may also monitor an abnormal state of the lung based on at least one of the pulmonary impedance, the movement of the thorax, and the RQ of the lung of the user based on the state information. For example, when the RQ measured when the user is lying is greater than a normal range or the pulmonary impedance measured when the user is lying is less than a normal range, the processor 250 may determine a possibility of occurrence of pulmonary edema in the lung of the user and transmit a signal indicating the possibility of occurrence of pulmonary edema.

The processor 250 may monitor the abnormal state of the heart and the lung of the user based on a result of comparing the bioinformation to a reference value of bioinformation that is classified by each posture and activity of the user. The reference value of the bioinformation that is classified by each posture and activity of the user may be a value stored in advance in the DB 205.

The transmitter-receiver 260 may transmit a result of the monitoring performed by the implantable monitoring device 200 to the external receiver 203 through the communication antenna 130.

The communication antenna 130 may transmit the result of the monitoring transmitted through the transmitter-receiver 260 to the external receiver 203 outside the implantable monitoring device 200. The external receiver 203 may be a user terminal, such as, for example, a wearable device and/or a smartphone. The external receiver 203 may continuously receive various sets of data including bioinformation measured by the implantable monitoring device 200 and/or an alarm indicating the abnormal state of the heart and the lung of the user. For example, when an abnormality is detected in the body of the user based on the data received from the implantable monitoring device 200, the external receiver 203 may notify the user of the detected abnormality. In addition, the external receiver 203 may store, in the external DB 205, the data received from the implantable monitoring device 200. The data accumulated in the DB 205 may be used for a future diagnosis. An operation of the implantable monitoring device 200 in relation to the external receiver 203 and the DB 205 will be described in detail with reference to FIG. 7.

Figure 3:
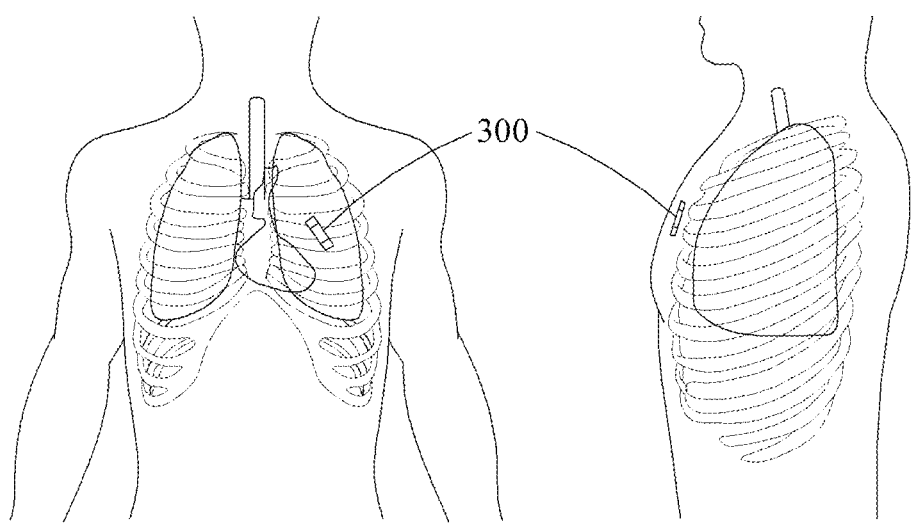
FIG. 3 illustrates an example of an implantation position in which an implantable monitoring device is to be implanted.

FIG. 3 illustrates an example of an implantation position in which an implantable monitoring device is to be implanted. Referring to FIG. 3, an implantable monitoring device 300 is implanted in skin of the thorax.

The implantable monitoring device 300 may be implanted into a subcutaneous fat layer within a preset distance from a heart of a user and a lung on one side of the user through, for example, an incision of skin, to increase specificity of a signal against relatively high resistance of skin. The lung on one side may be a lung present on a same side as where the heart is present. For example, when the heart of the user indicates a heart on a left side, the lung on one side of the user may indicate a lung on a left side. For another example, when the heart of the user indicates a heart on a right side, the lung on one side of the user may indicate a lung on a right side.

In an example, the implantable monitoring device 300 may be implanted in a portion adjacent to the lung, and thus measure more accurately a pulmonary impedance and minimize an external influence. The implantable monitoring device 300 may be implanted in a middle portion of the lung, and measure both an ECG and a pulmonary impedance. For example, the implantable monitoring device 300 may be implanted in a subcutaneous fat layers, 4 centimeters (cm) away from a center of sternum between third and fourth ribs, at an angle of 45°.

The implantable monitoring device 300 implanted in a body of the user may collect various sets of bioinformation. The implantable monitoring device 300 may monitor an abnormal state of the heart of the user that may be determined through a simple calculation of an R to R interval (RRI) of the ECG or heart rate, an abnormal movement of the heart, and the like. When the abnormal state is determined by the monitoring, the implantable monitoring device 300 may generate an alarm.

An external receiver may provide an accurate diagnosis by analyzing in detail data received from the implantable monitoring device 300 through a more complicated calculation or operation. For example, although, when the user moves excessively, an ECG or a movement of the heart of the user is measured as being abnormal by the excessive movement of the user, the external receiver may determine the data to be erroneous due to an external factor through a detailed analysis. In addition, data collected while the user is sleeping may be used as more reliable data.

When an alarm indicating a physical abnormality is generated by the implantable monitoring device 300 implanted in the body of the user or the external receiver, the implantable monitoring device 300 or the external receiver may transfer stored data of the user to a medical specialist or a doctor.

FIG. 4 illustrates an example of an impedance of a normal lung and an example of an impedance of a lung with pulmonary edema. FIG. 4 illustrates a current density in a normal lung 410 and a current density in a lung 430 with pulmonary edema.

Pulmonary edema is a condition where a fluid or water is abnormally accumulated outside a blood vessel of a lung, and may cause dyspnea, or a respiratory difficulty. Referring to FIG. 4, the current density in the lung 430 with pulmonary edema is higher than that of the normal lung 410 because the lung 430 has a greater amount of a fluid or water.

In addition, due to relatively high electrical conductivity in the lung 430 with pulmonary edema, a greater current flows towards the lung, and thus an impedance of the lung 430 with pulmonary edema is greater than that of the normal lung 410. In an example, an implantable monitoring device may determine a possibility of occurrence of pulmonary edema based on a difference in impedance between the normal lung 410 and the lung 430 with pulmonary edema, and generate an alarm.

Figure 5:
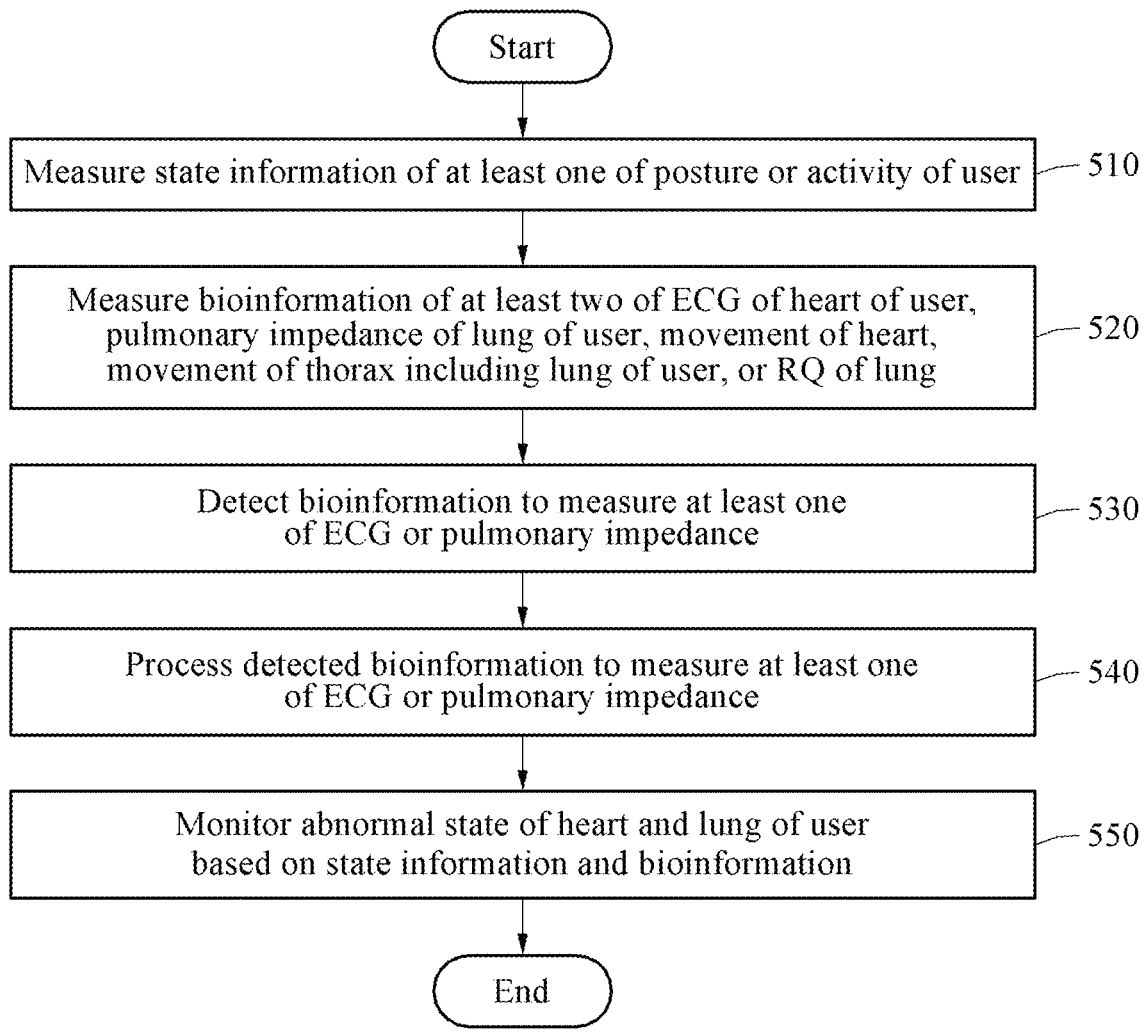
FIGS. 5 and 6 illustrate flowcharts of examples of a method of operating an implantable monitoring device.

FIG. 5 illustrates a flowchart of an example of a method of operating an implantable monitoring device. Referring to FIG. 5, in operation 510, an implantable monitoring device measures state information of at least one of a posture or an activity of a user. The implantable monitoring device may measure the state information of the at least one of the posture or the activity of the user, using motion sensors configured to sense a movement of the user, for example, a gyro sensor, a motion detector, and an acceleration sensor.

In operation 520, the implantable monitoring device measures bioinformation of at least two of an ECG of a heart of the user, a pulmonary impedance of a lung of the user, a movement of the heart, a movement of a thorax including the lung, or an RQ of the lung.

To measure at least one of the ECG or the pulmonary impedance in operation 520, the implantable monitoring device may sense a potential difference between electrodes at an implantation position in which the implantable monitoring device is implanted. The implantable monitoring device may sense the potential difference between the electrodes using a potential sensor, for example. In addition, to measure at least one of the movement of the heart, the movement of the thorax, or the RQ, the implantable monitoring device may sense a pressure at the implantation position. The implantable monitoring device may sense the pressure using a pressure sensor, for example.

In the example of FIG. 5, operations 510 and 520 are described as being performed in sequential order. However, examples are not limited to the illustrated example, and operations 510 and 520 may be performed simultaneously, or performed at a predetermined interval of time.

In operation 530, the implantable monitoring device detects bioinformation to measure at least one of the ECG and the pulmonary impedance. The implantable monitoring device may detect the bioinformation through two electrodes that are exposed to an outside of the implantable monitoring device.

In operation 540, the implantable monitoring device processes the detected bioinformation to measure the at least one of the ECG or the pulmonary impedance. In operation 540, the implantable monitoring device may obtain the pulmonary impedance by analyzing an AC voltage between the electrodes that is measured when an AC generated through a current generator is supplied. To measure the pulmonary impedance, the implantable monitoring device may apply a micro AC to a body or a tissue of the user and measure the AC voltage by the AC. In addition, in operation 540, the implantable monitoring device may obtain the ECG by analyzing an AC voltage between the electrodes measured when the AC is not supplied.

In operation 550, the implantable monitoring device monitors an abnormal state of the heart and the lung of the user based on the state information and the bioinformation. The implantable monitoring device may monitor the abnormal state of the heart of the user based on at least two of the ECG, the pulmonary impedance, or the movement of the heart, based on the state information. In addition, the implantable monitoring device may monitor the abnormal state of the lung of the user based on at least one of the pulmonary impedance, the movement of the thorax, or the RQ, based on the state information. The implantable monitoring device may transmit a result of the monitoring to an external receiver, and thus notify the user of the result of the monitoring.

For example, when there is an abnormality in a heart valve, there may be no symptom at first, but a stroke or infectious endocarditis may suddenly occur. Thus, when an abnormal movement of the heart is sensed through the pressure sensor, even though the ECG is in a normal range, the implantable monitoring device may notify the user of such through the external receiver to enable an early diagnosis. In addition, when the pulmonary impedance is out of a normal range and abnormally low, the implantable monitoring device may notify the user of a suspected case of pulmonary edema, and a doctor may determine whether the suspected case is related to cardiogenic or noncardiogenic pulmonary edema based on ECG and pressure sensor data that is continuously accumulated.

Since a disease such as heart failure and pulmonary edema is aggravated slowly, a symptom of the disease may not occur at first, but be developed and occur suddenly. Thus, by continuously obtaining data and monitoring a change in bioinformation, it is possible to predict and/or diagnose such disease.

Figure 6:
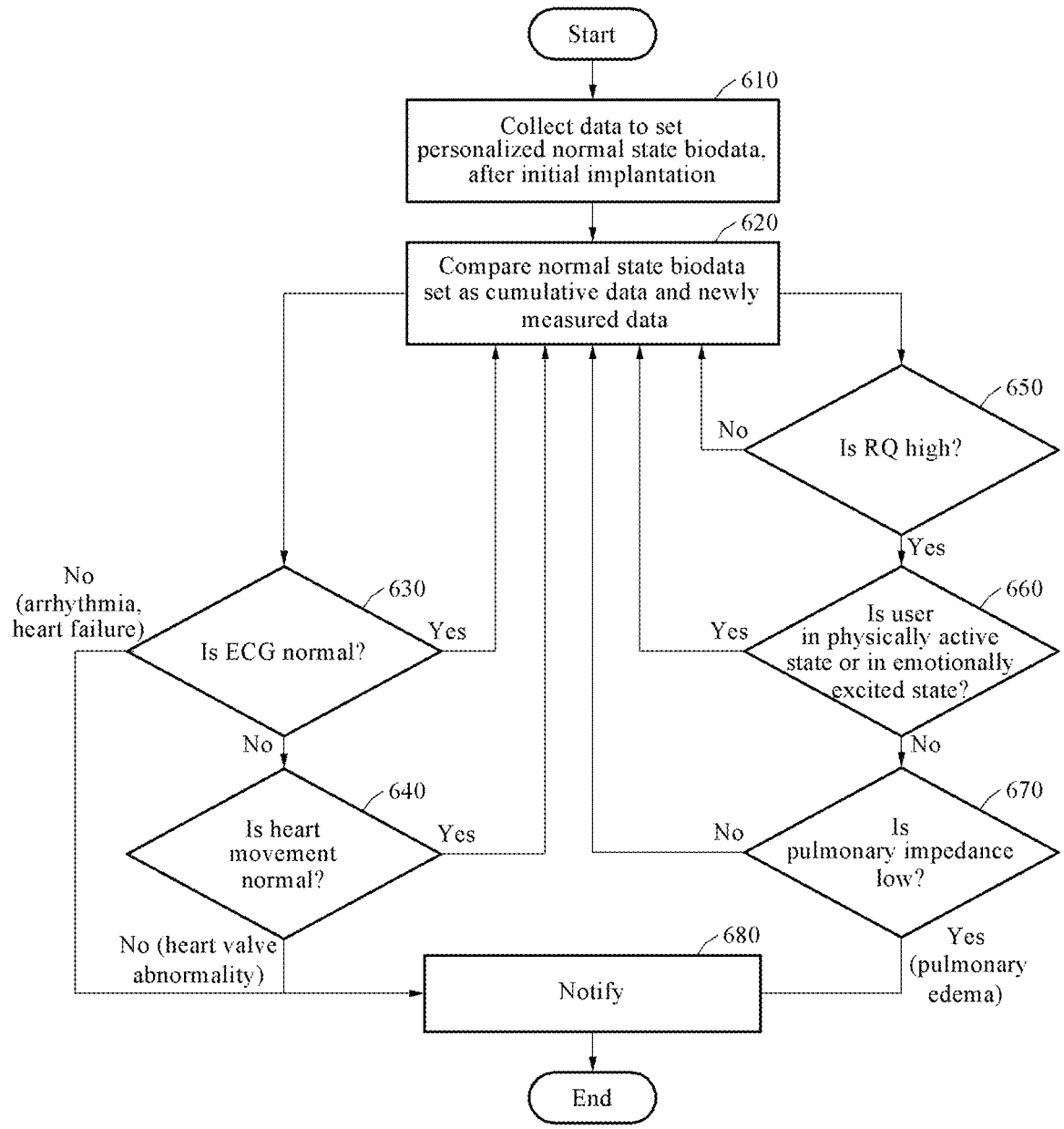

FIG. 6 illustrates a flowchart of another example of a method of operating an implantable monitoring device. Referring to FIG. 6, in operation 610, when an implantable monitoring device is initially implanted in a body of a user, the implantable monitoring device collects data to set personalized normal state biodata. Since normal state biodata differs from individual to individual, the implantable monitoring device may perform calibration to personalize the data collected in operation 610. For example, the implantable monitoring device may store bioinformation of each of an ordinary state, an exercise state, and a sleep state, and use the stored bioinformation to determine abnormality. The implantable monitoring device may set biodata for each personalized situation of the user through continuous data measurement. That is, the implantable monitoring device may set bioinformation for each posture and activity of the user. The set information or data may also be referred to as a reference value, information in a normal range, or normal state biodata.

In operation 620, the implantable monitoring device compares the normal state biodata set as cumulative data, and newly measured data.

In operation 630, the implantable monitoring device determines whether an ECG is normal as a result of the comparing in operation 620. Herein, that corresponding information is normal may be construed as being in a normal range. The implantable monitoring device may determine whether the ECG is normal by measuring an electrical and mechanical activity of a heart of the user using an ECG sensor and a pressure sensor, for example.

In operation 680, when the ECG is determined not to be normal in operation 630, the implantable monitoring device notifies an outside that the ECG is not normal.

In operation 640, when the ECG is determined to be abnormal in operation 630, the implantable monitoring device determines whether a movement of the heart of the user is normal. When the movement of the heart is determined to be normal in operation 640, the implantable monitoring device compares newly measured data to the normal state biodata in operation 620.

When the movement of the heart is determined not to be normal in operation 640, the implantable monitoring device determines occurrence of abnormality in a heart valve or occurrence of a valvular disease, and notifies the outside of such abnormality in operation 680.

In operation 650, the implantable monitoring device determines whether an RQ is high as the result of the comparing in operation 620. When the RQ is determined to be in a normal range in operation 650, the implantable monitoring device compares newly measured data to the normal state biodata in operation 620.

In operation 660, when the RQ is determined to be out of the normal range in operation 650 (for example, high), the implantable monitoring device determines whether the user is in a physically active state, for example, an amount of activity of the user is high, or the user is in an emotionally excited state. Here, an amount of activity may be predicted by heart rate. For example, when the amount of activity of the user is relatively great, the heart rate may be higher than that in the normal state biodata. Conversely, when the amount of activity of the user is relatively less, the heart rate may be lower than that in the normal state biodata. In addition, whether the user is in the emotionally excited state or not may be determined by whether bioinformation including a body temperature of the user changes rapidly within a short period of time compared to the amount of activity of the user.

When the amount of activity of the user is determined to be relatively great, or the user is determined to be in the emotionally excited state in operation 660, the implantable monitoring device compares newly measured data to the normal state biodata in operation 620.

In operation 670, when the amount of activity of the user is determined not to be relatively great, or the user is determined not to be in the emotionally excited state in operation 660, the implantable monitoring device determines whether a pulmonary impedance is less than a normal range. In operations 660 and 670, the implantable monitoring device measures the RQ and the pulmonary impedance using, for example, an impedance sensor and a pressure sensor, and determines whether the amount of activity of the user and/or the pulmonary impedance is in a normal range.

When the pulmonary impedance is determined not to be less than the normal range in operation 670, the implantable monitoring device compares newly measured data to the normal state biodata in operation 620.

When the pulmonary impedance is determined to be less than the normal range in operation 670, the implantable monitoring device determines a possibility of occurrence of pulmonary edema and notifies the outside of the possibility of occurrence of pulmonary edema in operation 680.

Figure 7:
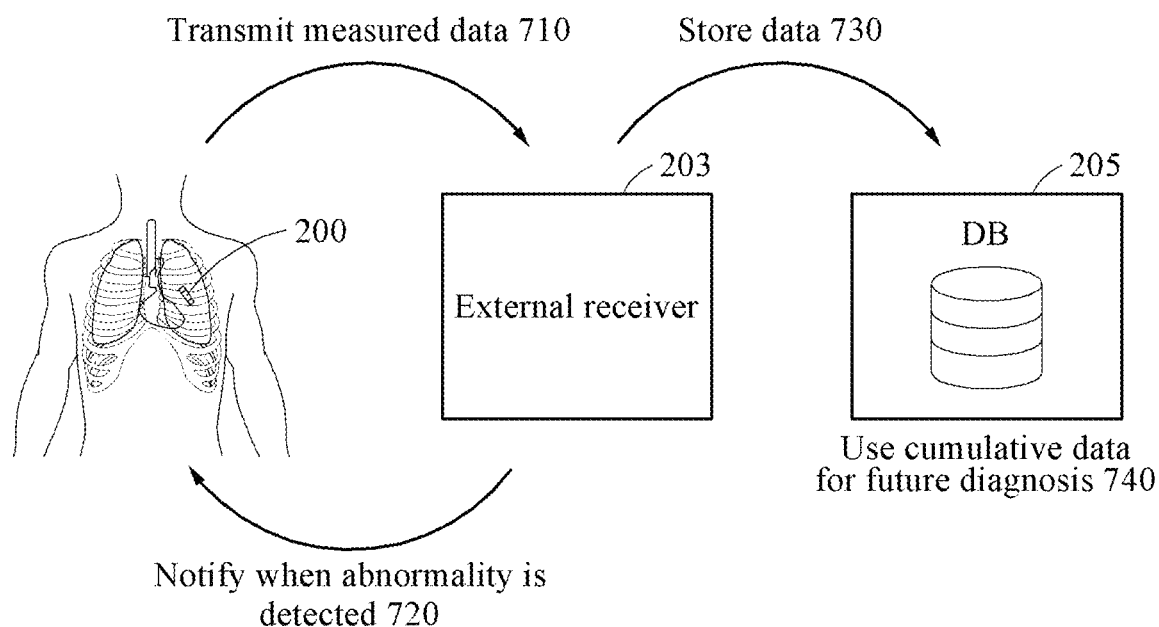
FIG. 7 illustrates an example of a method of operating an implantable monitoring device.

FIG. 7 illustrates an example of a method of operating an implantable monitoring device. In the example of FIG. 7, illustrated are an implantable monitoring device 200, an external receiver 203, and an external DB 205.

Referring to FIG. 7, in operation 710, the implantable monitoring device 200 that is implanted in a body of a user transmits measured data and/or a monitoring result to the external receiver 203. The implantable monitoring device 200 continuously transmits the measured data and/or the monitoring result to the external receiver 203. According to an example, a data obtainment and transmission period may be set in advance in the implantable monitoring device 200 to reduce battery consumption.

The external receiver 203 may be a user terminal or device, such as, for example, a wearable device and/or a smartphone. The measured data may include state information and bioinformation, for example. The external receiver 203 may continuously receive, from the implantable monitoring device 200, various sets of data including bioinformation and/or an alarm indicating an abnormal state of a heart and a lung of the user.

In operation 720, when an abnormality is detected from a body of the user based on the data received from the implantable monitoring device 200, the external receiver 203 notifies the user of the abnormality. For example, the external receiver 203 may diagnose arrhythmia based on an ECG measured by an ECG sensor, or a valvular abnormality of the heart based on an RQ measured by a pressure sensor. The external receiver 203 may make a diagnosis using both state information and bioinformation of the user. For example, when the user is running even though a heart rate of the user is higher than usual, the external receiver 203 may determine whether the heart is in an abnormal state or not by applying a normal heart rate corresponding to such running state.

In operation 730, the external receiver 203 cumulatively stores, in the external DB 205, data received from the implantable monitoring device 200. The external DB 205 may classify the data by each posture and activity of the user, and store therein the classified data.

In operation 740, the data accumulated in the external DB 205 is used for a future diagnosis. The data accumulated in the external DB 205 may be transmitted to a doctor and used for the doctor to make a diagnosis. For example, when the user feels an abnormality in the body of the user, the accumulated data may be used for comparison with bioinformation obtained when the user feels the abnormality, and to determine a cause of the abnormality. The doctor or a diagnosis device may make a diagnosis by predicting a disease based on a change of the bioinformation that is determined through the accumulated data. For example, the doctor may identify a cause of a symptom and a severity of the symptom based on accumulated ECG data, pressure sensor data, and pulmonary impedance data.

The implantable monitoring device, and other devices, apparatuses, units, modules, and other components described herein with respect to FIGS. 1, 2, and 7 are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 2-6 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions used herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An implantable monitoring device, comprising:
   first sensors configured to measure state information of one or both of a posture and an activity of a user;
   second sensors configured to measure bioinformation of two or more of an electrocardiogram (ECG) of a heart of the user, a pulmonary impedance of a lung of the user, a movement of the heart, a movement of a thorax including the lung, and a respiratory quotient (RQ) of the lung, the second sensors including a potential sensor configured to measure the pulmonary impedance and a pressure sensor configured to sense an abnormal movement of the heart and to measure the RQ;
   two electrodes configured to detect bioinformation to measure one or both of the ECG and the pulmonary impedance;
   an analog circuit configured to process the detected bioinformation to measure one or both of the ECG and the pulmonary impedance; and
   a processor configured to:
      monitor an abnormal state of the heart and the lung of the user based on the state information of the one or both of the posture and the activity of the user and the bioinformation of the two or more of the ECG, the pulmonary impedance, the movement of the heart, the movement of the thorax, and the RQ, determine whether the ECG is in a normal range or an abnormal range, detect abnormal movement of the heart via the pressure sensor, transmit a signal indicating the possibility of a stroke or infectious endocarditis in response to detecting an abnormal movement of the heart and determining that the ECG is in the normal range, and transmit the signal indicating the possibility of a stroke or infectious endocarditis in response to detecting an abnormal movement of the heart and determining that the ECG is in the abnormal range, determine the posture of the user is a lying posture based on the state information measured by the first sensors, and determine whether the RQ measured by the pressure sensor is greater than a normal RQ and determine whether the pulmonary impedance measured by the potential sensor is less than a normal range, and transmit a signal indicating a possibility of occurrence of pulmonary edema in the lung of the user in response to determining that the RQ is greater than the normal RQ and that the posture of the user is the lying posture and/or in response to determining that the pulmonary impedance is less than the normal range and that the posture of the user is the lying posture.

2. The implantable monitoring device of claim 1, wherein the processor is configured to:

monitor the abnormal state of the heart based on two or more of the ECG, the pulmonary impedance, and the movement of the heart based on the state information.

3. The implantable monitoring device of claim 2, wherein the processor is configured to:

detect that the movement of the heart and the RQ of the lung are out of a normal range based on the state information, and transmit a signal indicating a possibility of occurrence of a valvular disease in the heart of the user in response to the ECG being in the normal range and the movement of the heart and the RQ of the lung being out of a normal range.

4. The implantable monitoring device of claim 2, wherein the processor is configured to:

transmit a signal indicating a possibility of occurrence of heart failure in the heart of the user in response to determining that the pulmonary impedance is less than the normal range and that the posture of the user is the lying posture.

5. The implantable monitoring device of claim 1, wherein the analog circuit includes one or more of:

a current generator configured to generate an alternating current (AC) to measure the pulmonary impedance;

a voltage amplifier configured to amplify an AC voltage between the electrodes; and an analog-to-digital converter (ADC) configured to convert an analog signal based on the AC voltage to a digital signal based on a direct current (DC) voltage.

6. The implantable monitoring device of claim 5, wherein the analog circuit is configured to:

obtain the pulmonary impedance by analyzing an AC voltage between the electrodes measured when the AC generated through the current generator is supplied; and obtain the ECG by analyzing an AC voltage between the electrodes measured when the AC is not supplied.

7. The implantable monitoring device of claim 1, wherein the implantable monitoring device is implanted into a subcutaneous fat layer within a preset distance from the heart and the lung on one side of the user, wherein the potential sensor is configured to sense a potential difference between the electrodes at an implantation position in which the implantable monitoring device is implanted, to measure the one or both of the ECG and the pulmonary impedance, and wherein the pressure sensor is configured to sense a pressure at the implantation position to measure one or more of the movement of the heart, the movement of the thorax, and the RQ.

8. The implantable monitoring device of claim 1, wherein the processor is configured to:

monitor the abnormal state of the lung based on one or more of the pulmonary impedance, the movement of the thorax, and the RQ based on the state information.

9. The implantable monitoring device of claim 1, wherein the processor is configured to:

monitor the abnormal state of the heart and the lung of the user based on a result of comparing the bioinformation of the two or more of the ECG, the pulmonary impedance, the movement of the heart, the movement of the thorax, and the RQ, and a reference value of bioinformation of the two or more of the ECG, the pulmonary impedance, the movement of the heart, the movement of the thorax, and the RQ that is classified by each posture and activity of the user.

10. The implantable monitoring device of claim 1, further comprising:

a database configured to classify the bioinformation of the two or more of the ECG, the pulmonary impedance, the movement of the heart, the movement of the thorax, and the RQ by each posture and activity of the user, and store the classified bioinformation.

11. The implantable monitoring device of claim 1, wherein a measurement period of the first sensors and the second sensors is preset.

12. The implantable monitoring device of claim 1, further comprising one or more of:

a communication antenna configured to transmit a result of the monitoring;

a wireless power transfer antenna configured to receive energy wirelessly; and a power management circuit configured to charge a battery configured to supply power to the implantable monitoring device using the energy.

13. The implantable monitoring device of claim 1, wherein the first and second sensors include:

a motion sensor configured to measure one or both of the posture and the activity of the user;

an ECG sensor configured to measure an electrical signal of the heart of the user; and an impedance sensor configured to measure the pulmonary impedance of the lung of the user.

14. A method of operating an implantable monitoring device, the method comprising:

measuring state information of one or both of a posture and an activity of a user;

measuring bioinformation of two or more of an electrocardiogram (ECG) of a heart of the user, a pulmonary impedance of a lung of the user using a potential sensor, a movement of the heart using a pressure sensor, a movement of a thorax including the lung, and a respiratory quotient (RQ) of the lung using the pressure sensor;

detecting bioinformation to measure one or both of the ECG and the pulmonary impedance;

processing the detected bioinformation to measure the one or both of the ECG and the pulmonary impedance;

monitoring an abnormal state of the heart and the lung of the user based on the state information of the one or both of the posture and the activity of the user and the bioinformation of the two or more of the ECG, the pulmonary impedance, the movement of the heart, the movement of the thorax, and the RQ;

determining whether the ECG is in a normal range or an abnormal range;

detecting abnormal movement of the heart via the pressure sensor, transmitting a signal indicating the possibility of a stroke or infectious endocarditis in response to detecting an abnormal movement of the heart and determining that the ECG is in the normal range, and transmitting the signal indicating the possibility of a stroke or infectious endocarditis in response to detecting an abnormal movement of the heart and determining that the ECG is in the abnormal range;

determining the posture of the user is a lying posture based on the state information measured by the first sensors, and determining whether the RQ measured by the pressure sensor is greater than a normal RQ and determining whether the pulmonary impedance measured by the potential sensor is less than a normal range, and transmitting a signal indicating a possibility of occurrence of pulmonary edema in the lung of the user in response to determining that the RQ is greater than the normal RQ and that the posture of the user is the lying posture and/or in response to determining that the pulmonary impedance is less than the normal range and that the posture of the user is the lying posture.

15. The method of claim 14, wherein the implantable monitoring device is configured to be implanted into a subcutaneous fat layer within a preset distance from the heart and the lung on one side of the user, and includes two electrodes, and the measuring of the bioinformation of the two or more of the ECG, the pulmonary impedance, the movement of the heart, the movement of the thorax, and the RQ comprises:

sensing a potential difference between the electrodes at an implantation position in which the implantable monitoring device is implanted, to measure the one or both of the ECG and the pulmonary impedance; and sensing a pressure at the implantation position to measure one or more of the movement of the heart, the movement of the thorax, and the RQ.

16. The method of claim 14, wherein the processing of the bioinformation comprises:

obtaining the pulmonary impedance by analyzing an alternating current (AC) voltage between the electrodes measured when an AC generated through a current generator is supplied; and obtaining the ECG by analyzing an AC voltage between the electrodes measured when the AC is not supplied.

17. The method of claim 14, wherein the monitoring of the abnormal state of the heart and the lung of the user comprises:

monitoring the abnormal state of the heart based on two or more of the ECG, the pulmonary impedance, and the movement of the heart based on the state information.

18. The method of claim 14, wherein the monitoring of the abnormal state of the heart and the lung of the user comprises:

monitoring the abnormal state of the lung based on one or more of the pulmonary impedance, the movement of the thorax, and the RQ based on the state information.

19. A non-transitory computer-readable storage medium storing instructions that, when executed by one or more processors, cause the one or more processors to perform the method of claim 14.

* * * * *